United States Patent [19]

Russell

[11] 4,154,231

[45] May 15, 1979

[54] SYSTEM FOR NON-INVASIVE CARDIAC DIAGNOSIS

[76] Inventor: Robert B. Russell, 288 Heath St., Chestnut Hill, Mass. 02167

[21] Appl. No.: 848,932

[22] Filed: Nov. 23, 1977

[51] Int. Cl.$^2$ .............................................. A61B 5/02
[52] U.S. Cl. .............................. 128/663; 346/33 ME; 128/711; 128/700
[58] Field of Search ............. 346/33 ME; 128/2.05 E, 128/2.05 P, 2.05 Q, 2.05 R, 2.05 S, 2.05 T, 2.05 V, 2.05 Z, 2.06 G, 2.06 R, 2.06 V

[56] References Cited

U.S. PATENT DOCUMENTS

| | | | |
|---|---|---|---|
| 3,123,768 | 3/1964 | Burch et al. | 128/2.06 R |
| 3,292,018 | 12/1966 | Clynes | 128/2.05 R |
| 3,601,120 | 8/1971 | Massle | 128/2.05 S |
| 3,759,248 | 9/1973 | Valiquette | 128/2.05 R |
| 3,773,033 | 11/1973 | Rodbard et al. | 128/2.06 R |

OTHER PUBLICATIONS

Blumenfield et al., "Medical & Biological Engineering", vol. 9, No. 6, Nov. 1971, pp. 637–643.

*Primary Examiner*—William E. Kamm

[57] ABSTRACT

A system for detecting, quantizing, and displaying simultaneously on a single recording a wide panorama of cardiac diagnostic information including data inputs from EKG, phono-doppler, sound, and pulse; displaying each input in a distinctive color or form, in coordinates of time, frequency, and amplitude. A multi-channel recording system with an "instant replay" feature is employed to record simultaneously the respective inputs plus a timing pulse in separate channels, the timing pulse being generated by the periodic recurrence of a characteristic signal present in one of said inputs. A given sequence is selected for analysis and the recorded inputs for that sequence are replayed and fed to a high speed digital voltmeter-computer combination which dissects the wave form of the signals of each of said inputs separately and provides a read-out of the entire time, frequency, and amplitude content of all portions of the wave form of each input. A plotter transcribes the output of the computer three dimensionally, that is, in coordinates of time, frequency, and amplitude and distinguishes between the respective forms of data by presenting each in a distinctive color. A record of the output of the computer is also provided by means of a conventional computer print-out.

5 Claims, 1 Drawing Figure

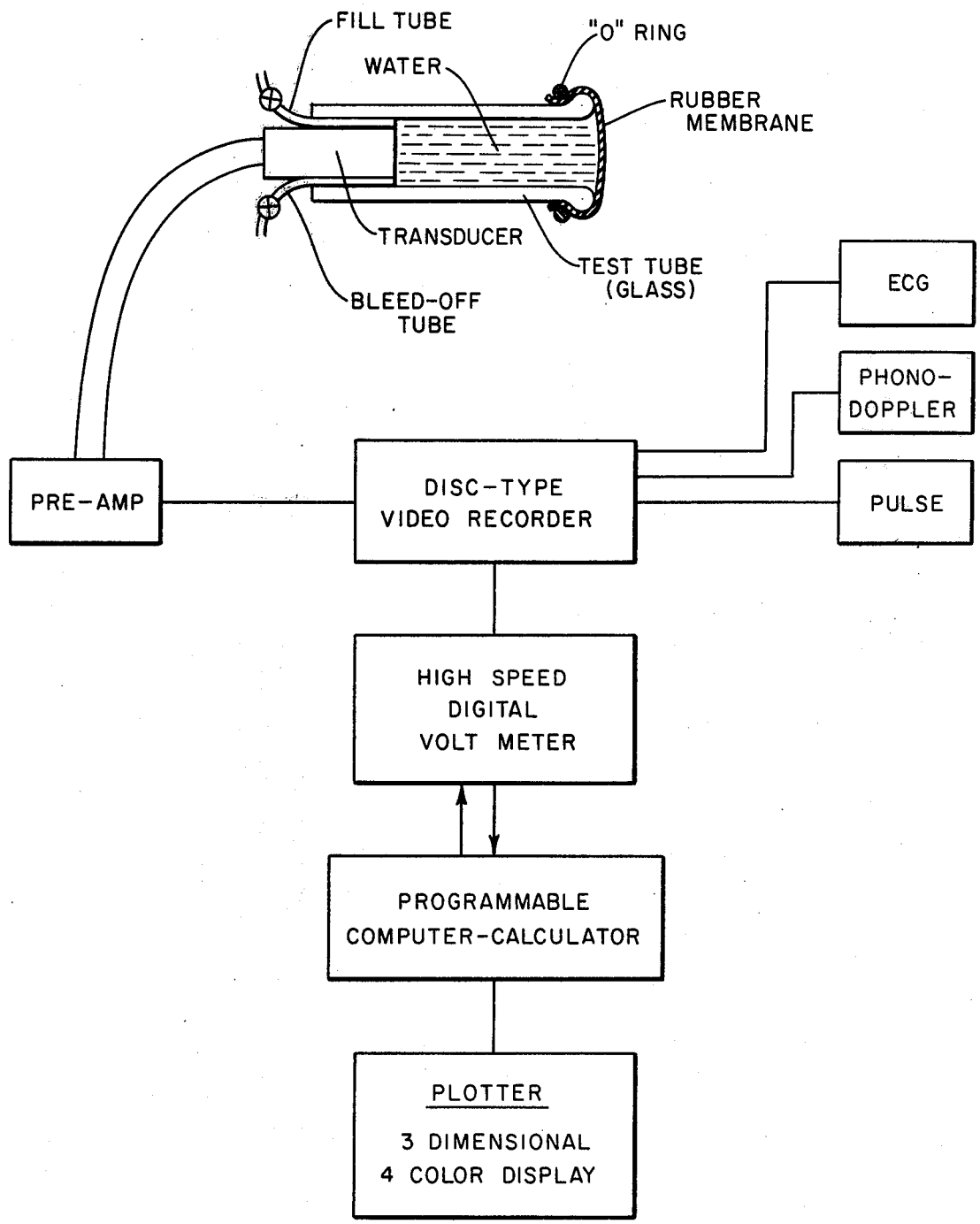

SYSTEM FOR NON-INVASIVE CARDIAC DIAGNOSIS

FIELD OF INVENTION

The present invention deals with non-invasive diagnostic techniques for the cardiovascular system. More particularly it relates to the analysis and quantization of cardiac disorders.

DESCRIPTION OF THE PRIOR ART

A great deal has been done in recent years to improve non-invasive techniques for the diagnosis and quantization of cardiac ailments. For example, at Massachusetts Institute of Technology extensive research has been expended on analyzing the origin and character of vascular murmurs and developing methods and equipments for characterizing and quantizing the sounds thereof, which methods they have labelled "phonoangiography." In fact, they have carried it far enough clinically so that they believe that in a high percentage of cases (83%) they can now determine, non-invasively, the cross-sectional area of a stenosis with an accuracy approaching that of radiographic methods ("Evaluation of Carotid Stenosis by Phonoangiography," N. E. Jour. of Med. 293: 1124–1128 (Nov. 1975)). The same group is also equipped with a small computer to process and correlate diagnostic data from other equipments such as ECG, phono-doppler and the like ("A Small Replicable Computer System for Clinical Analysis," Proc. Bio-Med Symp. 1976 Vol. 15 pp. 41–49).

Numerous other efforts to analyze and display frequency spectra of heart sounds and other data have also been made. For example, one effort to selectively detect and record sounds of differing frequencies is described in U.S. Pat. No. 3,171,406 to Baum et al; and displaying them three dimensionally (time, frequency, amplitude) is described in U.S. Pat. No. 3,188,645 to Trumpy et al. Commercially, Hewlett-Packard sell a device which selectively displays sounds of different frequencies (the HP 1541d), and Kay Elemetrics, Inc. sell a device for displaying heart sounds in three dimensions.

It still is a fact, however, that the problems of non-invasive cardiac diagnosis are far from solved, and that present day techniques suffer from serious draw-backs which if reduced or eliminated could lead to a highly desireable reduction in the need for invasive techniques for diagnosis.

In the area of phonoangiography, one area open for improvement relates to the range of frequencies being analyzed. For many years the frequency range considered to contain diagnostically significant sound has been from D.C. up to 2000 Hz. Thus, the recorded energy content of heart sounds (bruit) falls off very rapidly as the frequency increases above 1000 Hz. The problem with this, however, is that sounds above 1000 Hz and even above 2000 Hz are easily detectable by auscultation, and the fact remains that the equipments simply are not picking up the signals which the human ear can detect with ease. Since such signals are classifiable to physicians skilled in auscultation, it follows that equipments capable of doing likewise and recording same quantitatively, would provide a useful expansion of the data available for diagnosis. In addition, there is no reason to limit the detection of sounds to the audible range. Useful data may well exist in the ultrasonic range and a need exists for equipment capable of exploring same.

The duration of the sound bursts is also a major problem. Thus, if a sound burst at, say, 15 kHz remains active for only one or two milliseconds, the human ear might be able to hear it, but insufficient energy will pass through a conventional narrow band filter to permit the signal to be distinguished from the noise. The same applies to a signal comprising rapidly changing frequency. The equipments used in the prior art cited above have been incapable of detecting and accurately analyzing signals of extremely short duration, and, here again, the detection, quantization and display of same will at least make available to the diagnostician information not hitherto available to him.

Another area where an expansion of information may be feasible lies in the domain of the electro-magnetic waves detected by electrocardiography. The usual method is to display these electro-magnetic waves in the form of two dimensional traces in which only the components of lowest frequency and highest amplitude appear on each trace. It is known, however, that valuable information is present in the portions of the EKG frequency spectrum which are not displayed by the presently used EKG linear traces. The desireability of displaying such data and means for doing it are disclosed in U.S. Pat. No. 3,799,147 to Adolph et al. The Adolph device, however, makes only a crude separation of the EKG frequency components, and signals of extremely short duration are lost in the noise due to the filtering techniques used. Accordingly, a need still exists for equipment capable of presenting a more complete and more accurate picture of the EKG time, frequency and amplitude relationships.

In the phono-doppler area possibilities of detecting and displaying substantially more data than at present also exist. Existing "ultrasound" equipments such as those sold by USCI Company of Billerica, Massachusetts, and Brattle Instruments Corp. of Cambridge, Massachusetts, operate in the 2 MHz to 6 MHz range and provide doppler information in the form of low frequency beat notes derived from sound reflected from moving surfaces within the body. Typical uses for such equipments are in the detection of fetal heart beats and in estimating the velocity of blood flow. The total frequency content of such signals however, has not hitherto been extracted and displayed in time and amplitude coordinates for precision comparison with other detected events. As before, an ability to do so would provide an additional diagnostic tool which could have important ramifications.

Another major area where improvement is needed is in the collection, processing and presentation of the data in such a way that important distinctions can be recognized quickly and thereafter used effectively for diagnosis. Even with the relatively small amount of data presently being used (compared to the vast possibilities which exist), it is difficult to compare the traces and detect refinements of change. However, if the volume of data available for analysis is increased to the maximum possible, it would present a hopelessly complex maze and using present day equipments there would be no way to display and use the data conveniently and effectively. The use of multiple parallel oscillographs for the various data inputs as in conventional equipments is not adequate to handle more than a few inputs simultaneously, and it also suffers in terms of the precision of the comparisons one can make due to the practical impossibility of expanding the time base of such equipments sufficiently to provide the maximum definition of the time axis which the data inputs are capable of providing. Accordingly, an urgent need exists for a means capable of displaying a multiplicity of data from differing sources simultaneously and in an easily understandable way, and to do it with greater accuracy for the precision comparisons.

SUMMARY OF THE INVENTION

A general object of the present invention is to improve non-invasive techniques for cardiac diagnosis. More specifically, one object is to provide a means for detecting and displaying new diagnostic information in a manner which permits it to be used effectively. Another object is to render useful, data which, although already known to exist, has hitherto been considered useless due to a lack of adequate means for processing and displaying it. Still another objective is to display all data including that which is now being used, in a way which permits accurate and convenient simultaneous quantitative assessment thereof in terms of identification of the event, the location thereof, and the time, frequency, and energy content or amplitude of the detected signals therefrom.

These objectives are met in a preferred embodiment of the present invention by the combined use of means for detecting data comprising (a) a sensitive wide-band high frequency and low frequency transducer combination adapted to detect heart sounds covering the frequency range of 10 Hz to 300 kHz; (b) a conventional, multiple lead electrocardiograph; (c) conventional phono-doppler equipment, and (d) conventional pulse detection equipment. Next, the data from the detecting means are fed respectively to separate channels of a disc-type "instant replay" video recorder which simultaneously stores the wave form of each input including all frequency content thereof. Next a given time segment of a given heart beat is selected for analysis, and the recordation of that segment is replayed into a high speed digital voltmeter-computer combination (one input channel being processed at a time), with the computer being programmed to extract and print out the entire frequency content of the respective wave forms in relatively short "real time" increments. The output of the computer is fed to a plotter which is programmed to display the information three dimensionally, i.e. in coordinates of time, frequency, and amplitude. This is done preferably with the time coordinate horizontal, the amplitude coordinate vertical and the frequency coordinate at an angle so as to present the data in isometric perspective. The data from the respective channels is processed separately and in sequence with the recording head returning to the start of the time base for each channel so as to superimpose the data of each channel on the others. Different colors are used to distinguish the different types of data. A computer print-out is also made in order to provide a precise record of the digits which are represented graphically on the display.

A feature of the invention is that the digital voltmeter permits the detection of signals of extremely short duration over a very wide range of frequencies, and the computer permits their exact time, frequency and amplitude relationships to be detected and displayed. The plotter permits the display to be made three dimensionally and with the use of distinguishable colors. The total combination permits a very large amount of data to be displayed in one picture and in such a way that useful, accurate comparisons can be made. At the outset, it will be noted that such a display provides the diagnostician with all of the information he is currently using (as to any given heart beat), but that the data all appears in one place where it can be compared without having to look to other graphs. In addition, with such a display, none of the low frequency components of any of the inputs blanks out any of the weaker, higher frequency components, and these higher frequency components can be seen together with their time relationships to the others. The expansion of the time base permitted by such a display provides a greatly increased accuracy of time relationship determination. The computer print-out, however, provides a permanent record of the precise digital values for more detailed analysis if desired.

BRIEF DESCRIPTION OF THE DRAWING

In the single FIGURE, the various components of the system of the present invention are disclosed diagrammatically.

DETAILED DESCRIPTION OF THE INVENTION

The preferred embodiment of the present invention employs for the purpose of collecting the data, conventional EKG, phono-doppler, and pulse detection equipment such as the Hewlett-Packard No. 1514D "ECG-Phono-Pulse System." This system provides the full range of EKG data with multiple leads any one or more of which can be employed as desired. The transducers employed for sound and pulse detection in the HP-1514D system are suitable for data acquisition in the frequency range up to 2 kHz. The phono-doppler equipment can be an "Ultrasound" operating in the 2 MHz range sold by Brattle Instruments Corp. (Cambridge, Mass.), or an "Ultrasound" operating in the 5 MHz range sold by the USCI Company (Billerica, Mass.). The sound transducer for the higher frequencies up to 300 kHz may be a broad-band hydrophone sold by Linden Labs (State College, Pa). Preferably, it is mounted to a glass container filled with water, the container having a flexible membrane at one end for contact with the patient's skin. A suitable sound transmitting ointment is used between the membrane and the skin. All air bubbles are carefully evacuated from the container. All sound transducers are placed over the interspace between the ribs as near as possible to the location of the event to be detected.

A suitable video recorder to record the data may be the ARVIN-ECHO VDR-1R adapted for simultaneous recording of the respective inputs on separate channels. A large number of channels is available which permits the simultaneous, but separate recording of data from each EKG, sound, and phono-doppler lead.

The output of the recorder is fed to a Hewlett-Packard high speed digital voltmeter No. 3437A which is interfaced with a Hewlett-Packard desk-top computer No. 9825A which is programmed to call upon the voltmeter to sample the wave form of the inputs separately and sequentially in periods which can be as short as 0.2 milliseconds, proceeding through the entire heart beat portion under observation. The computer extracts the full frequency content of the wave form for each short period and transmits it to a Hewlett-Packard plotter No. 9872A which records the frequency content and the amplitude of each said period sequentially as the paper (or stylus) is advanced along the time base. The three dimensional display is created by employing the horizontal for time, the vertical for amplitude and an angle for frequency. This gives an impression of a flat plane with mountains on it. The perspective, however, is isometric. The stylus is returned to the starting point of the time base for the recordation of data from separate channels. A different colored ink is provided to distinguish the various forms of data. A computer print-out containing the data in digital form, is also provided by the computer.

It should be noted that the data collected in separate channels may, on occasion be recorded using the same color. Thus, the low frequency sound is recorded and processed separately from the high frequency sound, and the duration of the period thereof to be sampled by the recorder is substantially longer, but still the trace representing same can be recorded in the same colored ink without introducing confusion because it is basically the same type of information and the lower end of the spectrum will not interfere with the upper end.

OPERATION

In operation, the system of the present invention is used in parallel with conventional equipment and all signals therefrom are recorded by the disc recorder. In the preferred embodiment, the rise of the R wave of the EKG is used to generate a timing pulse to be used by the computer for synchronization of all readings.

A given heart beat or segment thereof is selected for analysis by reference to the conventional EKG traces. Next the video recorder is adjusted to replay that particular heart beat segment together with the timing pulse and to feed same rapidlyto the computer and voltmeter. The repetition rate of the replay depends upon the duration of the segment being analyzed. It can be as short as 33⅓ milliseconds with the equipment described. At this point the computer takes over and cycles through its complete routine with the plotter recording the output graphically and the computer providing the digital print-out.

The time required to complete a desired recordation depends upon the number of data channels needing analysis and the degree of accuracy desired. With the equipment described, accuracy is improved by repetition of the reading cycle and, therefore, improved accuracy sacrifices time. Under normal conditions, five minutes per recording is ample. This can be accelerated by the elimination of channels and a reduction in the accuracy demands.

The foregoing system makes possible the graphic display of the sounds of heart murmurs in a way never before available. With such a recording, the character of a murmur before an operation can be compared to the murmur following the operation which comparison is aided by the use of transparent or translucent recording paper so that the recordings can be laid one over the other. Thus, the character of the murmur of a given patient can also be followed from year to year to determine whether the condition is changing.

Experience will be needed to determine how many recordings need be taken to establish an adequate base, as well as to interpret and use the newly displayed data.

The inter-relationships between the detailed frequency changes of the phono-doppler data and the data from other events will also provide areas for analysis not heretofore used, and may permit the calculation of lumen diameters or the cross-sectional area of stenosed valves.

The recordations can be made quickly and stored. The video recorder is relatively small, portable, and convenient to use. In addition, it can be rented for short periods relatively inexpensively. Likewise, processing the data and making the graphic displays can be done at a central location for a relatively small charge per copy. Thus, the system can be made available for diagnosis without the necessity of tremendous capital investment.

In view of the low cost, it is envisioned that recordings as herein described will become a part of all routine cardiovascular examinations, and will serve to indicate the onset of arterial stenosis as well as the diagnosis of already critical conditions.

Various modifications of the preferred embodiment will now be apparent to those skilled in the art. The concept of taking a given heart beat or segment thereof for an individual, highly detailed simultaneous analysis of all forms of data relative thereto is basic to the invention. In addition the concept of the recordation of all of the collectible data relating thereto on a given single recording element is also basic because it makes possible the desired detailed analysis and simultaneous display. Moreover, the dissection of the selected heart beat segment in terms of amplitude, time and frequency in intervals down to 0.2 milliseconds, and over afrequency range of 10 Hz to 300 kHz, is likewise basic to the invention. In addition, a key feature is the presentation of a multiplicity of types of heart beat data on a single recording, three dimensionally and in different colors. I therefore intend to claim these aspects broadly.

Other ways are feasible, however, to do much the same thing. For example the display can be done on a video tube with amplitude being shown merely by changes of intensity of the beam, and the colors being provided by conventional color TV techniques. Recordation can be done by color photography. The same end result can be reached with a simple oscilloscope employing an intensity modulated trace and a camera arranged to move relative to the oscilloscope to establish a time axis between each transit of the trace along the frequency axis. The different colors can be recorded with such equipment by using color film and an appropriate color filter for each type of data. The display can also be done with a stylus using orthogonal coordinates for time and frequency and intensity of the trace for amplitude. Distinguishing between types of data can be done with hatch marks or other forms of distinctive trace deflections rather than colors. Therefore, since these and other similar changes of the preferred embodiment will now be obvious to those skilled in the art, it is not my intention to confine the invention to the precise form herein described but rather to limit it in terms of the appended claims.

I claim:

1. A system for collecting and displaying data for cardiac diagnosis, comprising means for transducing into electrical signals energy waves detectable at the suface of the body emanating from the cardiovascular system; broad band means for recording the output of said transducer corresponding to at least a segment of a given heart beat; a voltmeter for measuring and indicating the instantaneous voltage of electrical signals; means for repetitively feeding given portions of said recorded segment to said voltmeter; means for controlling said voltmeter to measure and indicate the instantaneous voltage of a succession of said portions sequentially and separately in extremely short intervals and for storing said indications to provide a composite stored replica of the given short portions of the wave form of said segment of said signals corresponding to a given short period of time which short period encompasses a multiplicity of said extremely short intervals; means for deriving from said stored replica the entire frequency content of said wave form for said short portion and for recording same graphically in coordinates of time, frequency and amplitude; and means for controlling the voltmeter controlling means to index successively to measure, store, derive and record the frequency contents of successive short portions of said wave form following said given short portion, whereby a three dimensional recordation of the time-frequency-amplitude content of said wave form is produced.

2. A system as defined in claim 1 further characterized by means for separately transducing into electrical signals a plurality of forms of said energy waves; means for recording said separately derived signals in separate recording channels; means for measuring and deriving the time, frequency, and amplitude content of each form as defined in claim 1 separately, and means for recording same one directly over the other on the coordinates on the same graph each in a self distinguishing form; whereby a composite picture of a plurality of forms of data is presented in a single graph.

3. A system as defined in claim 2 further characterized by said means for transducing said energy waves including EKG, sound, phono-doppler, and pulse wave transducers.

4. A system as defined in claim 3 further characterized by said sound transducer comprising means for transducing sounds from 10 Hz to at least 20 kHz.

5. A system as defined in claim 2 further characterized by means for displaying the respective forms in different colors.

* * * * *